United States Patent [19]

Iwasaki

[11] Patent Number: 5,099,007

[45] Date of Patent: Mar. 24, 1992

[54] LIGHT-SENSITIVE QUINONE DIAZIDE COMPOUND CONTAINING AN ALKYLIMIDAZOLE GROUP AND METHOD OF FORMING A PHOTORESIST USING SAID COMPOUND

[75] Inventor: Masayuki Iwasaki, Shizuoka, Japan

[73] Assignee: Fuji Photo Film Co., Ltd., Kanagawa, Japan

[21] Appl. No.: 443,409

[22] Filed: Nov. 30, 1989

[30] Foreign Application Priority Data

Dec. 2, 1988 [JP] Japan .................................. 63-305446

[51] Int. Cl.$^5$ ..................... G03F 7/022; C07C 245/00
[52] U.S. Cl. ..................... 534/557; 430/166; 430/192; 430/193; 430/326; 534/560; 534/556
[58] Field of Search ............... 430/193, 165, 192, 191, 430/166, 326; 534/556, 557, 560

[56] References Cited

U.S. PATENT DOCUMENTS

| | | | |
|---|---|---|---|
| 2,907,655 | 10/1959 | Schmidt et al. | 430/193 |
| 3,592,646 | 7/1971 | Holstead et al. | 430/193 |
| 3,956,262 | 5/1976 | Heyes et al. | 534/556 |
| 4,467,025 | 8/1984 | Goto et al. | 430/193 |
| 4,555,469 | 11/1985 | Erdmann et al. | 430/193 |
| 4,904,564 | 2/1990 | Chiong | 430/191 |

FOREIGN PATENT DOCUMENTS

| | | | |
|---|---|---|---|
| 626251 | 8/1961 | Canada | 430/193 |
| 632194 | 12/1961 | Canada | 430/193 |
| 218442A | 12/1984 | Japan | 430/193 |
| 729409 | 5/1955 | United Kingdom | 430/193 |

Primary Examiner—Charles L. Bowers, Jr.
Assistant Examiner—John S. Chu
Attorney, Agent, or Firm—Sughrue, Mion, Zinn Macpeak & Seas

[57] ABSTRACT

A light-sensitive compound is described, containing a quinonediazido group and an alkylimidazole group in the same molecule and which is solubilizable in an aqueous alkali solution upon irradiation with light, and a method of forming a photoresist using the light-sensitive compound. The compound is useful, for example, in production of print substrates and in chemical milling.

4 Claims, No Drawings

LIGHT-SENSITIVE QUINONE DIAZIDE COMPOUND CONTAINING AN ALKYLIMIDAZOLE GROUP AND METHOD OF FORMING A PHOTORESIST USING SAID COMPOUND

FIELD OF THE INVENTION

The present invention relates to a novel light-sensitive compound which can be used in production of printed wiring boards, chemical milling, and the like, and a method of forming a photoresist using the compound.

BACKGROUND OF THE INVENTION

Heretofore, as a method of forming a photoresist on the surface of a copper substrate, a method of coating a liquid photoresist, a method of laminating a dry film photoresist, and an electrodeposition coating method have been known. These methods, however, have respective problems.

The liquid photoresist coating method usually involves a photoresist composition that is generally dissolved in an organic solvent, coated on the surface of a copper substrate by a technique such as a spin coating method, a dip coating method, a screen printing method, a roller coating method, or a curtain coating method, and, thereafter, the organic solvent is evaporated to obtain a photoresist. In accordance with this method, although the production cost is low, when it is applied to a substrate for print wiring which has irregularities in the surface thereof, it is difficult to coat in a uniform thickness, which causes problems such as unevenness in development. Moreover, since an organic solvent is used, it is necessary to take precautions with respect to the dangers of explosion and other hazards. Furthermore, a sophisticated coating technique is demanded in order to obtain uniformity of the surface state, thickness, developing characteristics, sensitivity, and the like. Therefore, it is difficult to obtain high reproductivity.

For the foregoing reasons, the dry film photoresist method is mainly employed. Details of the liquid photoresist method and the dry film photoresist method are described, for example, in W. S. De Forest, *Photoresist*, 1975, McGraw Hill, New York.

In accordance with the dry film photoresist method, a relatively thick photoresist layer is laminated on the surface of a copper substrate, and thus a uniform photoresist layer can be formed relatively easily. Thus the dry film photoresist method has an advantage in that a pattern can be obtained with high precision. However, the dry film photoresist method also has some disadvantages in that productivity is low and production cost is relatively high.

The electrodeposition coating method is a method to deposit an aqueous dispersion of a photoresist composition on a copper substrate as an anode while passing electricity therethrough. This method is described in JP-A-62-262855 (the term "JP-A" as used herein means an "unexamined published Japanese patent application") and JP-A-62-262856 (corresponding to U.S. Pat. No. 4,845,012). Although this method has advantages of being high in resolving power and being low in production cost, because a photoresist in a thin film form can be obtained, it has a problem in respect of stability of the dispersion, and needs an apparatus for passing electricity.

SUMMARY OF THE INVENTION

An object of the present invention is to overcome the prior art problems encountered in formation of a photoresist on the surface of a copper substrate.

In accordance with the present invention, the problem due to an organic solvent is overcomed because the present invention does not use the organic solvent. Also in accordance with the present invention, a coating uniform in film thickness and markedly decreased in defects can be easily obtained and as compared with the dry film method, a pattern of higher resolving power can be obtained at lower production cost. Moreover, in the present invention, since a light-sensitive compound is used in a uniform aqueous solution, there is no problem of instability during storage of the dispersion, and since it is unnecessary to pass electricity, the formation of the photoresist can be carried out at very low production cost.

As a result of extensive investigations, it has now been found that a uniform photoresist layer is formed on the surface of a copper substrate by dipping the copper substrate in an acidic aqueous solution of a novel light-sensitive compound, i.e., a compound containing a quinonediazide group and an alkylimidazole group in the same molecule.

That is, the present invention relates to a light-sensitive compound containing a quinonediazido group and an alkylimidazole group in the same molecule and which is solubilizable in an aqueous alkali solution upon irradiation with light, and a method of forming a photoresist which includes a step of dipping a copper substrate in an acidic aqueous solution of the light-sensitive compound.

DETAILED DESCRIPTION OF THE INVENTION

Examples of the light-sensitive compounds of the present invention, containing a quinonediazide group and an alkylimidazole group in the same molecule, include compounds represented by formula (I) or (II):

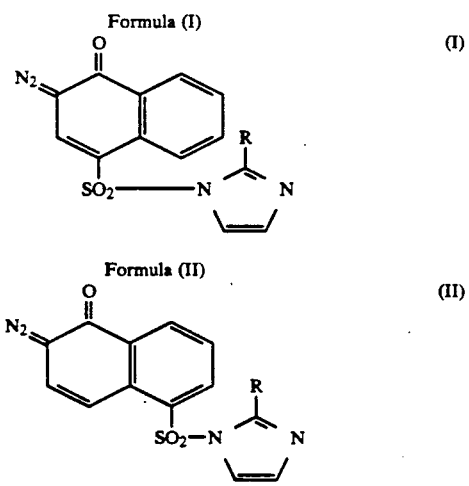

In formulae (I) and (II), R represents an alkyl group having from 6 to 20 carbon atoms, preferably from 11 to 16 carbon atoms.

Representative examples are 1-(naphthoquinone-1,2-diazido-(2)-4-sulfonyl)-2-hexylimidazole, 1-(naphthoquinone-1,2-diazido-(2)-5-sulfonyl)-2-hexylimidazole, 1-(naphthoquinone-1,2-diazido-(2)-4-sulfonyl)-2-heptylimidazole, 1-(naphthoquinone-1,2-diazido-(2)-5-sulfonyl)-2-heptylimidazole, 1-(naphthoquinone-1,2-diazido-(2)-4-sulfonyl)-2-octylimidazole, 1-(naphthoquinone-1,2-diazido-(2)-5-sulfonyl)-2-octylimidazole, 1-(naphthoquinone-1,2-diazido-(2)-4-sulfonyl)-2-nonylimidazole, 1-(naphthoquinone-1,2-diazido-(2)-5-sulfonyl)-2-nonylimidazole, 1-(naphthoquinone-1,2-diazido-(2)-4-sulfonyl)-2-decylimidazole, 1-(naphthoquinone-1,2-diazido-(2)-5-sulfonyl)-2-decylimidazole, 1-(naphthoquinone-1,2-diazido-(2)-4-sulfonyl)-2-undecylimidazole, 1-(naphthoquinone-1,2-diazido-(2)-5-sulfonyl)-2-undecylimidazole, 1-(naphthoquinone-1,2-diazido-(2)-4-sulfonyl)-2-dodecylimidazole, 1-(naphthoquinone-1,2-diazido-(2)-5-sulfonyl)-2-dodecylimidazole, 1-(naphthoquinone-1,2-diazido-(2)-4-sulfonyl)-2-tridecylimidazole, 1-(naphthoquinone-1,2-diazido-(2)-5-sulfonyl)-2-tridecylimidazole, 1-(naphthoquinone-1,2-diazido-(2)-4-sulfonyl)-2-tetradecylimidazole, 1-(naphthoquinone-1,2-diazido-(2) 5-sulfonyl)-2-tetradecylimidazole, 1-(naphthoquinone-1,2-diazido-(2)-4-sulfonyl)-2-pentadecylimidazole, 1-(naphthoquinone-1,2-diazido-(2)-5-sulfonyl)-2-pentadecylimidazole, 1-(naphthoquinone-1,2-diazido-(2)-4-sulfonyl)-2-hexadecylimidazole, 1-(naphthoquinone-1,2-diazido-(2)-5-sulfonyl)-2-hexadecylimidazole, 1-(naphthoquinone-1,2-diazido-(2)-4-sulfonyl)-2-heptadecylimidazole, 1-(naphthoquinone-1,2-diazido-(2)-5-sulfonyl)-2-heptadecylimidazole, 1-(naphthoquinone-1,2-diazido-(2)-4-sulfonyl)-2-octadecylimidazole, 1-(naphthoquinone-1,2-diazido-(2)-5-sulfonyl)-2-octadecylimidazole, 1-(naphthoquinone-1,2-diazido-(2)-4-sulfonyl)-2-nonadecylimidazole, 1-(naphthoquinone-1,2-diazido-(2)-5-sulfonyl)-2-nonadecylimidazole, 1-(naphthoquinone-1,2-diazido-(2)-4-sulfonyl)-2-eicosylimidazole, 1-(naphthoquinone-1,2-diazido-(2)-5-sulfonyl)-2-eicosylimidazole, and the like.

Of these compounds, 1-(naphthoquinone-1,2-diazido-(2)-5-sulfonyl)-2-undecylimidazole and 1-(naphthoquinone-1,2-diazido-(2)-5-sulfonyl)-2-heptadecylimidazole are particularly preferred.

Formation of a photoresist on a copper substrate using the novel light-sensitive compound of the present invention can be carried out by the following method.

At least one light-sensitive compound is dissolved to prepare an acidic aqueous solution (pH: 0 to 6) in the concentration of from 0.1 to 25 wt %, preferably from 0.5 to 10 wt %. In this acidic aqueous solution maintained at a temperature of from 15° to 60° C., preferably from 20 to 50° C., the copper substrate is dipped. The dipping time can be determined appropriately depending on the required film thickness. Usually, the dipping time is preferably from 1 to 20 minutes. If a solution having a high concentration and a high temperature is used, the deposition speed is increased.

The copper substrate used in the present invention includes, for example, a copper leaf, or a substrate such as a paper, a phenol resin and an epoxy resin board intensified with glass fiber, each in which a copper leaf is adhered on the surface thereof.

The film thickness of the photoresist thus obtained is usually in the range of from 0.5 to 100 μm in a dry condition. As a photoresist, the film thickness in the range of from 2 to 60 μm is preferred.

After deposition of the compound in a layer form, the copper substrate is removed from the aqueous solution and washed with water, and then upon removal of water contained in the layer by a heating technique such as hot air, a photoresist is obtained.

Using the photoresist thus obtained, a printed board or the like can be produced, for example, by the following conventional method.

That is, after exposure with active light through a pattern mask, exposed areas are removed with a developer to expose the surface of copper. The exposed copper surface is dissolved by applying an etching solution and the resist is removed with an acidic releasing agent to obtain a circuit pattern.

As the active light, light in the wavelength range of from 300 to 600 nm, and preferably from 350 to 450 nm, is used. As a light source, sun light, a mercury lamp, a xenon lamp, an arc lamp, etc., can be used. The exposure time is usually in a range of from 1 second to 5 minutes, and preferably in a range of from 7 seconds to 2 minutes, although it may vary depending on the intensity of the light source, the distance between the light source and the resist, and so on.

Development is carried out, e.g., by spraying alkali developer onto the exposed photoresist surface As the alkali developer, an aqueous solution of sodium carbonate, sodium hydroxide, potassium hydroxide or the like, or ammonia water and the like can be used.

As the etching solution, any one can be used as long as it is alkaline, and a copper ammonia solution is preferably used.

In peeling the resist, a strongly acidic aqueous solution, or an organic solvent compatible with water, or a mixture thereof, can be used. A concentrated aqueous solution of hydrochloric acid, or a 5 wt % aqueous solution of hydrochloric acid containing from 10 to 30 wt % of methanol, is preferred.

The following examples are further illustrative of the present invention but should by no means be construed as limiting its scope.

EXAMPLE 1

1-(Naphthoquinone-1,2-diazido-(2)-5-sulfonyl)-2-undecylimidazole was prepared by the following method.

2.7 g of naphthoquinonediazido-5-sulfonyl chloride and 2.2 g of 2-undecylimidazole were dispersed in 10 g of methyl ethyl ketone. To this mixture, a solution of 1.01 g of triethylamine in 10 g of methyl ethyl ketone was dropped at room temperature, and after 3 hours, the reaction solution was poured into 500 g of water.

The powdery solid thus obtained was filtered off, washed with water and then recrystallized from 200 ml of methanol, to obtain 3.6 g of 1-(naphthoquinone-1,2-diazido-(2)-5-sulfonyl)-2-undecylimidazole. Properties of this compound are shown below.

m.p.: from 104° to 105° C.

Elemental Analysis:

|   | Found (%) | Calculated (%) |
|---|---|---|
| C | 63.14 | 63.41 |
| H | 6.37 | 6.65 |
| N | 12.17 | 12.33 |
| S | 6.95 | 7.05 |

Using the compound thus obtained, printed wiring boards were produced by the following method.

A light-sensitive solution having the following formulation was prepared in a vat.

| | |
|---|---|
| 1-(Naphthoquinone-1,2-diazido-(2)-5-sulfonyl)-2-undecylimidazole | 0.1 g |
| Glacial acetic acid | 2 g |
| Concentrated hydrochloric acid | 10 g |
| Water | 8 g |

A copper covered laminate with copper plated through holes was dipped in the above light-sensitive solution at room temperature and the vat was agitated. After five minutes, the laminate was removed from the vat and dipped in a beaker filled with water for one minute, and then removed and dried for 2 minutes in an oven maintained at 100° C. A photoresist layer attached to the surface of copper was low in tackiness, and the film thickness was 5 μm.

A mask with a circuit pattern was superposed on the laminate carrying thereon the photoresist layer, and light exposure of 400 mJ/cm² was applied for 20 seconds by the use of a super high pressure mercury lamp (3 kW).

The laminate was placed in a 2% aqueous solution of sodium hydroxide, developed for one minute while applying vibration, and washed with water. In this way, the circuit pattern was reproduced with high reproductivity. The resolving power was 4 μm.

The resolving power as defined herein means the minimum line width of a photo mask when the line images obtained by developing after exposing through a photo mask having various line patterns (line/space = 1/1) are separately formed.

Subsequently, exposed copper was dissolved by etching with a copper ammonia etchant (A-Process, produced by Meltex Co., Ltd.) at 40° C. for 140 seconds, and, on peeling the resist by dipping in concentrated hydrochloric acid, a circuit pattern of copper was obtained with high fidelity.

EXAMPLE 2

In the same manner as in Example 1, except that 1-(naphthoquinone-1,2-diazido-(2)-5-sulfonyl)-2-heptadecylimidazole was used as a light-sensitive compound, a photoresist layer was formed on a laminate and evaluated. The developing power was 4 μm.

What is claimed is:

1. A light-sensitive compound represented by Formula (I):

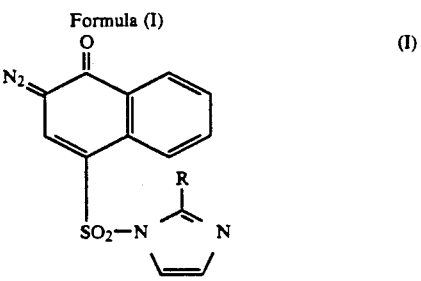

Formula (I)

wherein R represents an alkyl group having from 6 to 20 carbon atoms, which light-sensitive compound is solubilizable in an aqueous alkali solution upon irradiation with light.

2. A light-sensitive compound represented by Formula (II):

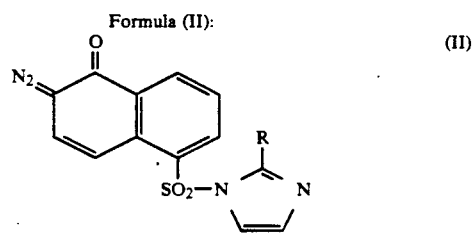

Formula (II):

wherein R represents an alkyl group having from 6 to 20 carbon atoms, which light-sensitive compound is solubilizable in an aqueous alkali solution upon irradiation with light.

3. A light-sensitive compound as in claim 2, wherein said compound is 1-(naphthoquinone-1,2-diazido-(2)-5-sulfonyl)-2-undecylimidazole.

4. A light-sensitive compound as in claim 2, wherein said compound is 1-(naphthoquinone-1,2-diazido-(2)-5-sulfonyl)-2-heptadecylimidazole.

* * * * *